(12) United States Patent
Jeon

(10) Patent No.: US 6,689,348 B1
(45) Date of Patent: Feb. 10, 2004

(54) METHOD AND COMPOSITION FOR HAIR TREATMENT

(75) Inventor: Young Chuel Jeon, Busan (KR)

(73) Assignee: MO21 International Ltd., Mississauga (CA)

( * ) Notice: Subject to any disclaimer, the term of this patent is extended or adjusted under 35 U.S.C. 154(b) by 25 days.

(21) Appl. No.: 10/185,213

(22) Filed: Jun. 28, 2002

(51) Int. Cl.$^7$ ................ A61K 7/06; A61K 35/78; A61K 39/385
(52) U.S. Cl. ............ 424/74; 424/70.1; 424/401; 424/725; 424/757; 424/773; 514/880
(58) Field of Search ............... 424/401, 70.1, 424/74, 725, 757, 773; 514/880

(56) References Cited

FOREIGN PATENT DOCUMENTS

| CN | 1167610 A | * | 12/1997 |
| DE | 10050669 A1 | * | 4/2002 |
| JP | 01199904 A | * | 8/1989 |
| JP | 01213215 A | * | 8/1989 |
| KR | 2000031349 A | * | 6/2000 |

* cited by examiner

Primary Examiner—Thurman K. Page
Assistant Examiner—Marina Lamm
(74) Attorney, Agent, or Firm—McDermott, Will & Emery

(57) ABSTRACT

A composition for treating hair includes an effective amount of a herbal extract extracted from Angelica and Astragali Radix. The herbal extract is prepared by adding water to these herbs in dried form, and heating the resulting liquid for 1 to 8 hours, at a temperature of about 90–200 degrees Celsius. An amine compound, preferably diethanol amine, or a combination of triethanol amine and dioctyl sodium sulfosuccinate, is added to the herbal extract. Benzoic acid, dissolved in ethanol, is also added to the herbal extract, together with water. The resulting solution is fermented between 12 to 24 hours, in an ultrasonic fermentation apparatus operating at about 15 KHz. A method for the treatment of hair loss includes applying to the scalp the above-described composition.

19 Claims, No Drawings

METHOD AND COMPOSITION FOR HAIR TREATMENT

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to a composition and method for treating hair; and more particularly for treating hair loss, for supplying nutrients to hair, and for cleansing the scalp.

BACKGROUND OF THE INVENTION

Treatments for hair loss and other scalp and hair disorders have long been sought. Hair loss occurs in a variety of situations, including but not limited to male pattern baldness (androgenetica alopecia), diseases accompanied by skin lesions or tumors, nutritional disorders, and internal secretion disorders. The mechanisms causing hair loss are very complicated, and thus not easily amenable to well-defined causes. In some instances, however, hair loss can be attributed to causes including aging, genetic disposition, activation of hormones, loss of blood supply to hair follicles, and scalp abnormalities.

Hair loss is a widespread ailment. At present, people suffering from hair loss constitute about 25% of the population in Asia, and about 30% of the population in America and Europe. A wide variety of products for the stimulation of hair growth have been developed and commercialized in numerous countries. These products include medical, pharmaceutical, cosmetic, and industrial products. Two hair-growth stimulants have been officially approved by the FDA: Rogaine™ (minoxidil), a composition that lowers blood pressure and is adapted to be applied on the skin; and Propecia™ (finasteride), a composition that is also used to treat thyroid-related obesity.

Many of the products currently in the market have been touted for their purported efficacy, and their constituent components have been widely advertized. A number of the products utilize compositions based on chemical compounds, while others are based on extracts from naturally-occurring herbs. For example, U.S. Pat. No. 4,874,791 describes a hair-growing agent containing as an effective ingredient an aliphatic carboxylic acid having an odd number of carbon atoms or a derivative thereof; U.S. Pat. No. 4,759,231 discloses a hair tonic composition that contains an extract from a Chinese herb, dong chong xia cao.

In many cases, however, it has been found that the efficacy of the hair treatment products and the actual results obtained by the consumers do not match or live up to the reported or suggested results. Continued research and experimentation in this area is therefore necessary.

An improved product for preventing hair loss and promoting hair growth is desirable.

SUMMARY OF THE INVENTION

The present invention is directed to a method and composition for treating hair, based on extracts of Asian herbs that are subjected to ultrasonic fermentation.

A composition for treating hair include effective amounts of an herbal extract, and particularly an extract extracted from a species of Angelica, and from Astragali Radix. The herbal extract is prepared by adding water to effective amounts of the herbs, and heating the resulting liquid for 1 to 8 hours, at a temperature of 90–200 degrees Celsius. An amine compound, preferably diethanol amine, or a combination of triethanol amine and dioctyl sodium sulfosuccinate, is added to the herbal extract. Benzoic acid, dissolved in ethanol, is then added to the herbal extract, together with water. The resulting solution is fermented between 12 to 24 hours, in an ultrasonic fermentation apparatus operating at about 15 KHz.

A method for the treatment of hair loss includes applying to the scalp the composition described above.

A method of preparing a hair treatment composition includes preparing a herbal extract of Angelica and Astragali Radix, and filtering the herbal extract. The method includes combining the filtered herbal extract with an amine compound selected from the group consisting of diethanol amine, and triethanol amine combined with dioctyl sodium sulfosuccinate. The method includes adding a solution of benzoic acid (dissolved in ethanol) to the filtered herbal extract, together with water. The method includes fermenting in an ultrasonic fermenting apparatus the resulting solution.

DETAILED DESCRIPTION

The present invention features an improved hair treatment composition that has proved to be exceptionally effective in applications that include, but are not limited to, promoting hair growth, preventing hair loss, supplying nutrients to hair, and cleansing the scalp.

A hair treatment composition, prepared in accordance with one embodiment of the present invention, includes an extract of the herbs Angelica, and Astragali Radix. Any of a variety of species of Angelica can be used to prepare the extract, including but not limited to: Angelicae Gigantis Radix, Angelica Cutiloba Kitagawa, Angelica Archangelica, Angelica Sinensis, Angelica Uchiyamana, Ligusticum Acutilobum Krragawa, and Angelica Gigas.

To prepare about 20 (twenty) liters of the hair treatment composition, about 200 grams to about 2000 grams of the chosen species of Angelica, and about 5 grams to about 100 grams of Astragali Radix is required, in dried form. An extract of these dried herbs is prepared by adding water to the dried herbs, and heating the resulting liquid for about 1 hour to about 8 hours, at a temperature from about 90 degrees Celsius to about 200 degrees Celsius. The resulting extract is filtered.

One of the following agents or compounds is added to the filtered extract-solution, preferably in the indicated amounts (although other amounts of the agents are also within the scope of the present invention): 1) diethanol amine (about 30 grams to about 220 grams); or 2) a combination of triethanol amine (about 30 grams to about 220 grams) and dioctyl sodium sulfosuccinate (about 20 grams to about 150 grams). The addition of the amine agents results in regulating the pH level of the hair treatment composition, so that the end product is characterized by a pH level of between about 7.5 to about 9.0.

Benzoic acid is then dissolved in ethanol. Preferably, between about 5 grams to about 20 grams of benzoic acid is used in 800 milliliters of ethanol. This solution is added to the filtered extract solution from the previous step, together with water. The amount of water is adjusted, until the total volume of the filtered extract solution reaches about 20 liters.

The resulting solution is fermented for about 12 hours to about 24 hours in an ultrasonic fermenting apparatus, to produce the desired hair treatment product. The ultrasonic fermenting apparatus is characterized by a frequency between about 10 KHz to about 20 KHz, preferably 15 KHz.

The hair treatment product of the present invention has proved to be extremely effective in preventing hair loss, promoting hair growth, and supplying nutrients to hair. User reaction to the product has been exceptionally positive. Commercialization of the composition disclosed above promises to be very helpful to patients suffering from loss of hair, and from scalp irritations. Studies conducted over a number of years have shown that continued use of this product is completely harmless, and devoid of side effects.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A composition for the treatment of hair, consisting essenhally of:
    a) an effective amount of an herbal extract extracted from a species of Angelica and from Astragali Radix;
    b) a compound selected from the group consisting of i) diethanol amine, and ii) a combination of triethanol amine and dioctyl sodium sulfosuccinate; and
    c) a solution of benzoic acid dissolved in ethanol.

2. A composition according to claim 1, wherein said composition is obtained by adding said compound, said solution of benzoic acid, and water to said extract after filtering said extract, and by fermenting the resulting solution for a time period in an ultrasonic fermenting apparatus.

3. A composition according to claim 2, wherein said time period is between about 12 hours to about 24 hours.

4. A composition according to claim 2, wherein said ultrasonic fermenting apparatus is characterized by a frequency of about 15 KHz.

5. A composition according to claim 2, wherein said ultrasonic fermenting apparatus is characterized by a frequency of from about 10 KHz to about 20 KHz.

6. A composition according to claim 1, wherein said species of Angelica is selected from the group consisting of Angelicae Gigantis Radix, Angelica Cutiloba Kitagawa, Angelica Archangelica, Angelica Sinensis, Angelica Uchiyamana, Ligusticum Acutilobum Krragawa, and Angelica Gigas.

7. A composition according to claim 1, wherein the amount of said species of Angelica is between about 200 grams to about 2000 grams by weight in dried form, per 20 liters of said composition.

8. A composition according to claim 1, wherein the amount of said Astragali Radix is between about 5 grams to about 100 grams by weight in dried form, per 20 liters of said composition.

9. A composition according to claim 1, wherein said solution of benzoic acid comprises between about 5 grams to about 20 grams of benzoic acid dissolved in about 800 milliliters of ethanol.

10. A composition according to claim 1, wherein said extract of Angelica and Astragali Radix is obtained by adding water to said species of Angelica and to Astragali Radix, and heating the resulting liquid at an effective temperature, during a time interval.

11. A composition according to claim 10, wherein said effective temperature is from about 90 degrees Celsius to about 200 degrees Celsius.

12. A composition according to claim 10, wherein said time interval is from about 1 hour to about 8 hours.

13. A composition according to claim 1, wherein said composition is characterized by a pH of about 7.5 to about 9.0.

14. A method for the treatment of hair loss, comprising applying to the scalp a composition consisting essenhally of a) a herbal extract extracted from a species of Angelica and from Astragali Radix; b) an amine compound selected from the group consisting of i) diethanol amine, and ii) a combination of triethanol amine and dioctyl sodium sulfosuccinate; and c) a benzoic acid solution dissolved in ethanol;

wherein said composition is prepared by adding said amine compound, said benzoic acid solution, and water to said herbal extract, and fermenting the resulting liquid in an ultrasonic fermenting apparatus.

15. A method of preparing a hair treatment composition, comprising:
    a) preparing an herbal extract of Angelica and Astragali Radix;
    b) filtering said extract;
    c) combining said filtered extract with a compound selected from the group consisting of i) diethanol amine, and ii) triethanol amine combined with dioctyl sodium sulfosuccinate;
    d) adding water, and a solution of benzoic acid dissolved in ethanol, to the product obtained in step c); and
    e) fermenting in an ultrasonic fermenting apparatus the solution resulting from step d).

16. A method according to claim 15, wherein the step of preparing said herbal extract comprises the steps of:
    a) adding water to dried forms of said species of Angelica and said Astragali Radix; and
    b) heating the liquid resulting from step a) at an effective temperature, during a time interval.

17. A method according to claim 16, wherein said effective temperature is from about 90 degrees to about 200 degrees Celsius.

18. A method according to claim 16, wherein said time interval is from about 1 hour to about 8 hours.

19. A composition according to claim 1, wherein the amount of said diethanol amine is about 30 grams to about 220 grams, the amount of said triethanol amine is about 30 grams to about 220 grams, and the amount of said dioctyl sodium sulfosuccinate is amout 20 grams to about 150 grams.

* * * * *

UNITED STATES PATENT AND TRADEMARK OFFICE
CERTIFICATE OF CORRECTION

PATENT NO. : 6,689,348 B1 Page 1 of 1
DATED : February 10, 2004
INVENTOR(S) : Young Chuel Jeon It is certified that error appears in the above-identified patent and that said Letters Patent is hereby corrected as shown below:

<u>Column 3,</u>
Line 23, from the beginning, delete "essenhally", and insert thereof -- essentially --;

<u>Column 4,</u>
Line 17, after "consisting", delete "essenhally", and insert thereof -- essentially --;

Signed and Sealed this

Fifteenth Day of June, 2004

JON W. DUDAS
*Acting Director of the United States Patent and Trademark Office*